(12) United States Patent
Boling et al.

(10) Patent No.: US 9,216,285 B1
(45) Date of Patent: Dec. 22, 2015

(54) LEADLESS IMPLANTABLE MEDICAL DEVICE HAVING REMOVABLE AND FIXED COMPONENTS

(71) Applicant: PACESETTER, INC., Sylmar, CA (US)

(72) Inventors: Carl Lance Boling, San Jose, CA (US); Gene A. Bornzin, Simi Valley, CA (US); Yelena Nabutovsky, Mountain View, CA (US); Avi Fischer, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/575,933

(22) Filed: Dec. 18, 2014

(51) Int. Cl.
| | |
|---|---|
| A61N 1/36 | (2006.01) |
| A61N 1/05 | (2006.01) |
| A61N 1/372 | (2006.01) |
| A61N 1/378 | (2006.01) |
| A61N 1/365 | (2006.01) |
| A61B 5/024 | (2006.01) |

(52) U.S. Cl.
CPC ............ *A61N 1/059* (2013.01); *A61B 5/02444* (2013.01); *A61N 1/365* (2013.01); *A61N 1/3787* (2013.01); *A61N 1/37264* (2013.01)

(58) Field of Classification Search
None
See application file for complete search history.

(56) References Cited

U.S. PATENT DOCUMENTS

| | | | |
|---|---|---|---|
| 2011/0270340 A1* | 11/2011 | Pellegrini et al. | 607/9 |
| 2013/0303872 A1* | 11/2013 | Taff et al. | 600/374 |
| 2013/0325081 A1* | 12/2013 | Karst et al. | 607/25 |
| 2014/0128935 A1* | 5/2014 | Kumar et al. | 607/27 |

* cited by examiner

*Primary Examiner* — Brian T Gedeon
*Assistant Examiner* — Ankit Tejani

(57) ABSTRACT

A leadless implantable medical device (IMD) may include an electrode, a housing, and an energy transfer component. The housing retains a pulse generator configured to provide stimulation energy for delivery to a tissue of interest, a power supply, a memory storing programmable instructions, and a processor communicatively coupled to the memory. The processor is responsive to the programmable instructions to control operation of the leadless IMD. The electrode is securely affixed to the tissue of interest. The housing includes first and second body portions mated to one another at a detachable interface. The electrode is coupled to the second body portion. The energy transfer component is distributed between the first and second body portions and is configured to convey at least one of stimulation energy or sensed signals across the detachable interface when the first and second body portions are mated to one another.

11 Claims, 7 Drawing Sheets

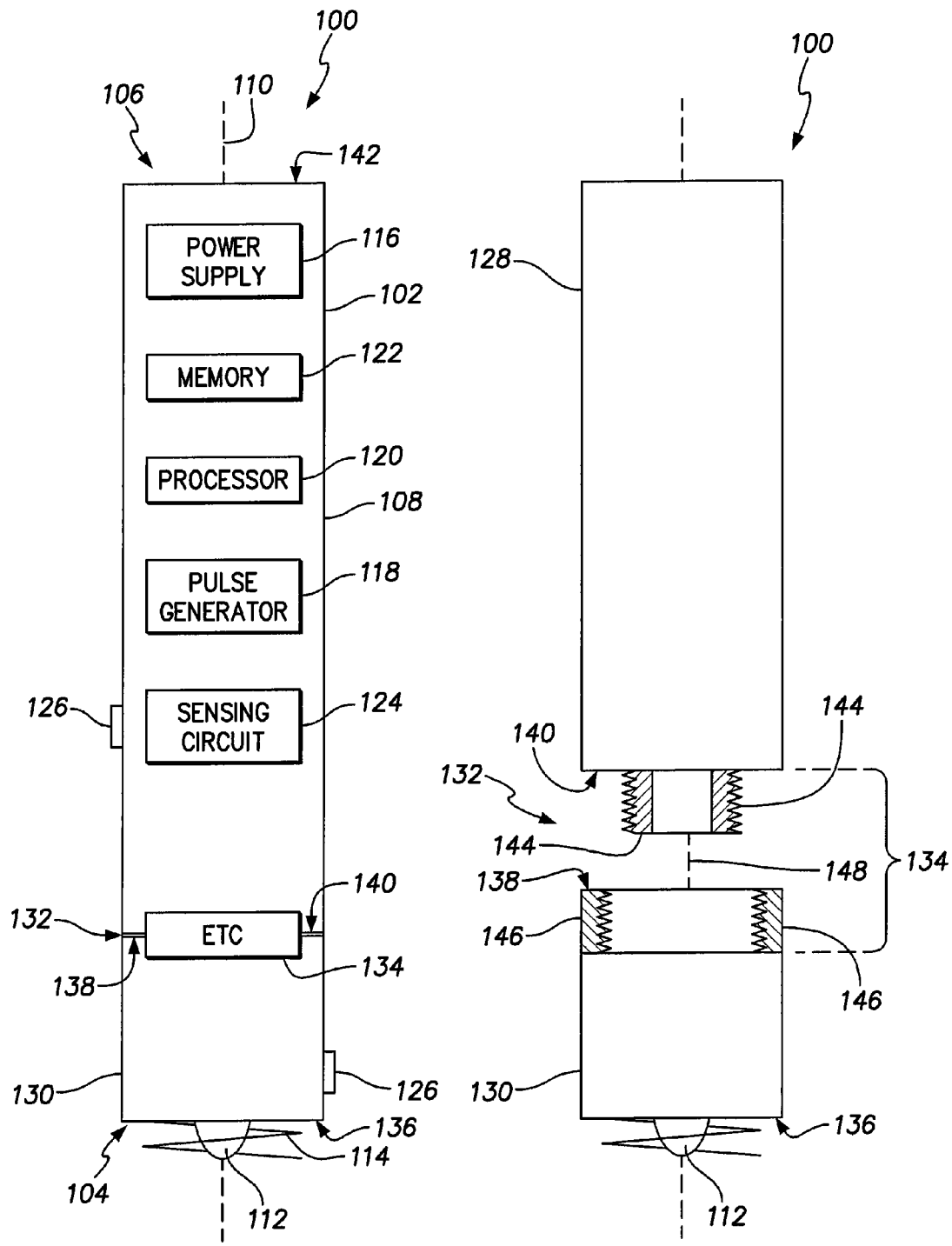

LEADLESS IMPLANTABLE MEDICAL DEVICE HAVING REMOVABLE AND FIXED COMPONENTS

FIELD OF THE INVENTION

Embodiments of the present invention generally relate to implantable medical devices and more particularly to leadless intra-cardiac medical devices that provide stimulation energy to and/or monitor intrinsic electrical activity through a tissue of interest.

BACKGROUND

Some known implantable medical devices (IMD) for cardiac applications, such as pacemakers, are used to deliver pacing pulses to a cardiac chamber to induce a depolarization of that chamber, which is followed by mechanical contraction of that chamber, when a patient's own intrinsic rhythm fails. The IMD further includes sensing circuits that sense electrical activity for the detection of intrinsic cardiac events such as intrinsic atrial depolarizations (detectable as P waves) and intrinsic ventricular depolarizations (detectable as R waves). By monitoring electrical activity, the IMD is able to determine the intrinsic rhythm of the heart and provide stimulation pacing pulses that force atrial and/or ventricular depolarizations at appropriate times in the cardiac cycle to help stabilize the electrical rhythm of the heart.

Some known IMDs utilize one or more electrically-conductive leads that extend from a remotely-located canister or pulse-generator and traverse blood vessels and cardiac chambers to affix connected electrodes to the heart. The housing or canister, referred to as a "can", has electronics and a power source. The can, including the power and processing circuitry, and a portion of the leads are located outside of the patient's heart, and the power and data signals are relayed to and from the heart via the leads.

Since the leads traverse the vascular system and connect to the heart from the remote can, infectious organisms, most commonly bacteria, may be introduced into the patient's systemic circulation and heart through the leads, thereby increasing the risk of infection within the heart. Additionally, because the IMD is located outside of the heart, most often in a pre-pectoral pocket, the patient may be susceptible to Twiddler's syndrome. Twiddler's syndrome is typically characterized by a subconscious, inadvertent, or infrequently deliberate rotation of the IMD within a subcutaneous pocket created in the patient into which the IMD is implanted. This results in lead retraction and wrapping around the IMD and as a result, leads may dislodge from the endocardium. Further consequences include stimulation of the diaphragm, phrenic nerve, pectoral muscles, or brachial plexus as a result of the displaced lead. In addition to the foregoing complications, the presence of leads may be associated with and/or cause a number of additional complications.

To mitigate the limitations and complications associated with transvenous leads and the associated IMD, smaller sized devices configured for intra-cardiac implant without the need for transvenous leads have been proposed. These devices, termed "leadless pacemakers", are devoid of leads that pass out of the heart to another component, such as a can located outside of the heart. The entire device is configured to be attached to the heart. Thus, the power source and the processing circuitry are contained within the device that is attached to the heart. The leadless pacemakers include electrodes that are affixed directly to the can of the device, instead of being separated by a distance traversed by one or more leads. Each leadless pacemaker is capable of local pacing and sensing in the chamber of the heart where it is implanted.

The leadless pacemakers that have been proposed thus far offer limited functional capability. For example, when the power source (e.g., battery) is depleted and/or the processing circuitry needs to be updated, the entire device must be removed from the heart. Removing the pacemaker device from the myocardial tissue of the heart may be difficult and may damage the surrounding cardiac and/or vascular tissue. In some cases, the removal may even tear the myocardial tissue. Removing the leadless pacemaker from a fixated position may be complicated by fibrosis around the fixation mechanism, which occurs when tissue grows around and at least partially envelops the fixation system of the leadless pacemaker after attaching the pacemaker to the tissue wall.

Once the depleted leadless pacemaker is removed, additional problems may be encountered when implanting a new replacement leadless pacemaker. For example, when implanting the replacement pacemaker, a preferred location to affix the device is in the same location as the previous pacemaker due to stable sensing and pacing values and knowledge that the location is stable to accommodate the implanted device. However, identifying the previous location may be very difficult and the presence of fibrosis at the site of previous fixation may limit accessibility to this exact location. In addition, implanting a new device in the same location as the device that was extracted may be difficult due to tissue damage caused by the extraction. The removal process may render the underlying tissue and substrate less stable, less efficient for pacing, and more prone for perforation during the implantation of the replacement pacemaker. Locating the replacement pacemaker at a different location than the previous pacemaker may change the pacing and sensing thresholds, requiring additional steps to calibrate the sensing circuitry and adjust the pacing circuitry, while still risking reduced performance due to a sub-optimal and less stable implant location. Accordingly, it is important to avoid detaching the leadless pacemaker electrode from the tissue wall on which it is mounted, which would disturb the surrounding tissue as well as the pacing and sensing thresholds.

SUMMARY

In an embodiment, a leadless implantable medical device (IMD) is provided that includes a pulse generator configured to provide stimulation energy for delivery to a tissue of interest, a power supply, a memory storing programmable instructions, and a processor communicatively coupled to the memory. The processor is responsive to the programmable instructions to control operation of the leadless IMD. The leadless IMD further includes an electrode, a housing, and an energy transfer component. The electrode is configured to be securely affixed to the tissue of interest. The housing retains the pulse generator, the power supply, the memory, and the processor. The housing includes first and second body portions mated to one another at a detachable interface. The electrode is coupled to the second body portion. The energy transfer component is distributed between the first and second body portions at the detachable interface. The energy transfer component is configured to convey at least one of stimulation energy or sensed signals across the detachable interface when the first and second body portions are mated to one another.

In an embodiment, a method is provided for use with a leadless implantable medical device (IMD). The method includes providing the leadless IMD to a tissue of interest. The leadless IMD has a housing including first and second body portions mated to one another at a detachable interface.

The second body portion is coupled to an electrode. The leadless IMD further includes an energy transfer component distributed between the first and second body portions at the detachable interface. The energy transfer component is configured to convey at least one of stimulation energy or sensed signals across the detachable interface when the first and second body portions are mated to one another. The method also includes affixing the electrode to the tissue of interest to anchor the leadless IMD to the tissue of interest. The method further includes disengaging the first body portion from the second body portion at the detachable interface. The second body portion remains affixed to the tissue of interest after the first body portion is disengaged therefrom.

BRIEF DESCRIPTION OF THE DRAWINGS

FIG. 2 illustrates a side view of the LIMD of FIG. 1 according to an embodiment.

FIG. 3 illustrates a side view of the LIMD showing a removable component disengaged from a fixed component according to an embodiment.

DETAILED DESCRIPTION

Figure 1:
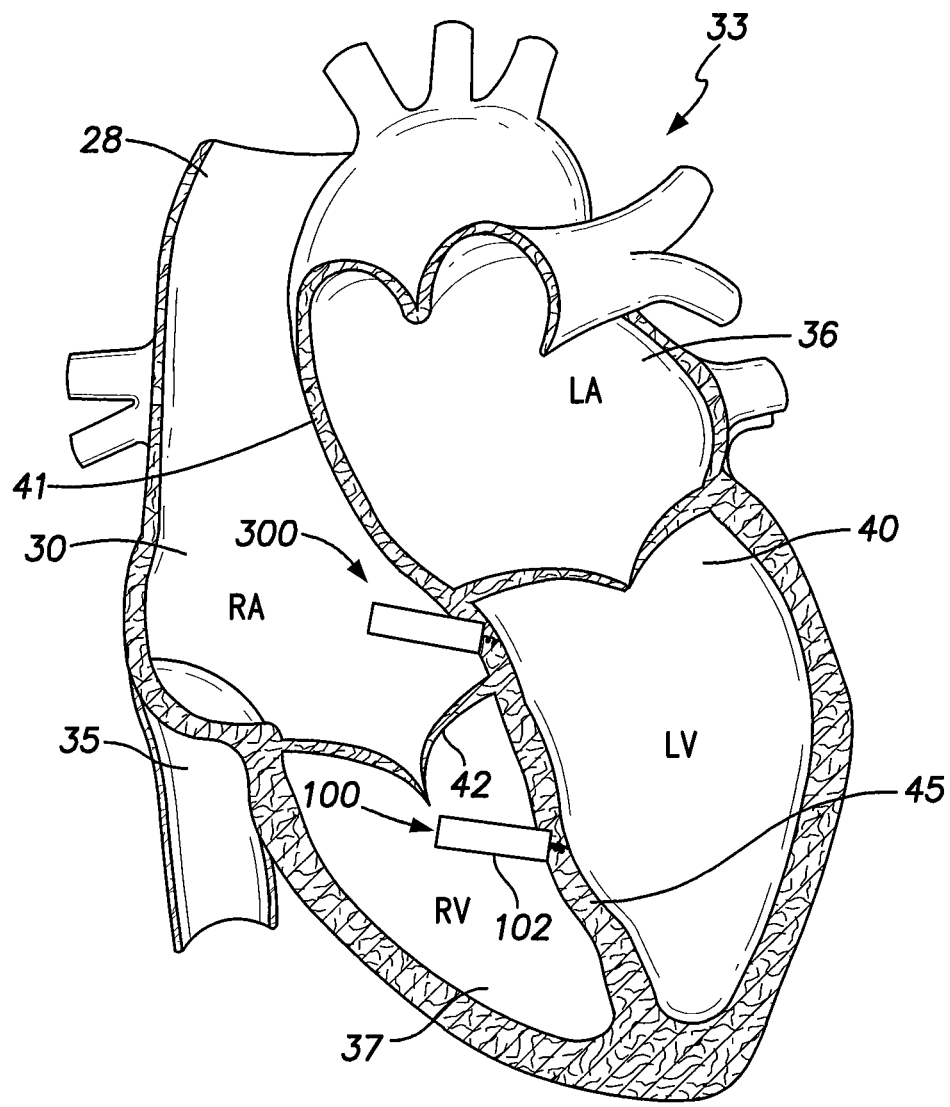
FIG. 1 illustrates a sectional view of a patient's heart with a leadless intra-cardiac medical device (LIMD) implanted therein.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware and circuitry. Thus, for example, one or more of the functional blocks (e.g., processors or memories) may be implemented in a single piece of hardware (e.g., a general purpose signal processor or a block or random access memory, hard disk, or the like). Similarly, the programs may be standalone programs, may be incorporated as subroutines in an operating system, may be functions in an installed imaging software package, and the like. It should be understood that the various embodiments are not limited to the arrangements and instrumentality shown in the drawings.

As used herein, the term "leadless" generally refers to an absence of electrically-conductive leads that traverse vessels or other anatomy outside of the intra-cardiac space, while "intra-cardiac" means generally, entirely within the heart and associated vessels, such as the superior vena cava (SVC), inferior vena cava (IVC), coronary sinus (CS), coronary veins (CV), pulmonary arteries, and the like.

One or more embodiments generally relate to leadless implantable medical devices (LIMD) and systems, such as pacemakers and implantable cardioverter-defibrillators (ICDs) that attach to intra-cardiac endocardial tissue to provide pacing and/or sensing. One or more embodiments relate, in particular, to such devices and systems that have a removable component and a fixed component, and methods for use therewith. Some of the embodiments relate to a removable component of the LIMD that is detachable from the fixed component, such that when the LIMD is mounted to intra-cardiac tissue, the removable component may be disengaged from the fixed component without dismounting the fixed component from the intra-cardiac tissue. The removable component includes a power supply and/or control circuitry that controls at least some operation of the LIMD, such that removing the removable component allows for replacement with a replacement removable component that includes a new power supply and/or upgraded control circuitry. Thus, in one or more embodiments described herein, the LIMD may be configured to switch power supplies and/or control circuitry when necessary or desirable without disturbing the mounting of the fixed component of the LIMD to the intra-cardiac tissue.

FIG. 1 provides a sectional view of a patient's heart 33 and shows a leadless implantable medical device (LIMD) 100. The LIMD 100 has been placed through the superior vena cava 28 into the right atrium 30 of the heart 33. FIG. 1 also shows the inferior vena cava 35, the left atrium 36, the right ventricle 37, the left ventricle 40, the atrial septum 41 that divides the two atria 30, 36, and the tricuspid valve 42 between the right atrium 30 and the right ventricle 37.

The LIMD 100 is formed in accordance with an embodiment. The LIMD 100 may represent a pacemaker, a cardiac resynchronization device, a cardioverter, a defibrillator, or the like. The LIMD 100 comprises a housing 102 configured to be implanted entirely within a single local chamber of the heart 33, such as entirely and solely within the right atrium 30 or the right ventricle 37, for example. Optionally, the LIMD 100 may be implanted entirely and solely within the left atrium 36 or the left ventricle 40, which may require modified implant methods compared to implantation in the right atrium 30 or the right ventricle 37.

The chamber in which the LIMD 100 is implanted may be referred to as the "local" chamber. The local chamber includes a local chamber wall that is physiologically responsive to local activation events originating in the local chamber. The local chamber is at least partially surrounded by local wall tissue that forms, contains, or constitutes at least part of a conduction network for the associated chamber. For example, during normal operation, the wall tissue (myocardium) of the right atrium contracts in response to an intrinsic local activation event that originates at the sinoatrial (SA) node, and the resulting conduction propagates along the myocytes that comprise atrial wall tissue. For example, tissue of the right atrium chamber wall in a healthy heart follows an organized and repetitive conduction pattern, through depolarization and repolarization, that originates at the SA node and moves downward through the right atrium reaching the atrioventricular (AV) node.

As shown in FIG. 1, the local chamber in which the LIMD 100 is implanted is the right ventricle 37. For example, the LIMD 100 is mounted or fixated to the tissue wall of the right ventricle 37 along the septum 45 that divides the right ventricle 37 from the left ventricle 40. The septum 45 wall tissue in the right ventricle 37 may behave physiologically differently than the non-septum ventricular wall tissue. An electrode on the LIMD 100 engages tissue that is part of the conductive network of the right ventricle 37. Optionally, the LIMD 100 is implanted in an area near different regions of tissue that follow the conductive pattern of different chambers of the heart. The LIMD 100 may have another electrode that engages tissue that is part of the conductive network of another chamber, such as the right atrium 30. In other embodiments, the LIMD 100 may be implanted at a different location within the right ventricle 37 or within a different intra-cardiac chamber. Alternatively, multiple LIMDs may be implanted into the patient's heart 33 within different chambers or different segments of the same chamber.

As described further herein, a portion of the housing 102 of the LIMD 100 is configured to be removed from a remaining portion of the housing 102 without dismounting the remaining portion from the wall tissue of the local chamber, such as right atrium 30 shown in FIG. 1. The remaining portion of the housing 102 is the portion that mounts directly to the wall tissue. The removable portion may be completely explanted from the heart 33, and a new replacement component may be implanted into the local chamber and coupled to the remaining portion that is fixed to the wall tissue. The remaining portion is not moved relative to the wall tissue during the replacement of the removable portion, so the fixation between the LIMD 100 and the wall tissue of the local chamber is not disturbed. As a result, the risk of damaging the wall tissue when removing and replacing the LIMD 100 is reduced as is the risk for device dislodgement. In addition, the risk of not being able to relocate a replacement LIMD in the same location as the previous LIMD 100 (which affects the pacing and sensing thresholds) is also reduced.

FIG. 2 illustrates a side view of the LIMD 100 according to an embodiment. The illustrated LIMD 100 includes a schematic representation of some internal components of the LIMD 100. The housing 102 of the LIMD 100 includes a first, mounting end 104, an opposite second end 106, and an intermediate shell 108 extending between the first end 104 and the second end 106. The shell 108 is elongated and tubular in shape and extends along a longitudinal axis 110. The mounting end 104 mounts to tissue of an intra-cardiac wall within a chamber of the heart.

The mounting end 104 includes an electrode 112 securely attached thereto and projecting outward from the mounting end 104. The electrode 112 is configured to deliver stimulation energy to a tissue of interest. As used herein, "tissue of interest" refers to intra-cardiac tissue that the LIMD 100 is configured to monitor and provide stimulation energy to. In the illustrated embodiment, the LIMD 100 is configured to be affixed directly to the tissue of interest, as described below. The electrode 112 may be a cathode electrode that is actively fixated to the myocardium. The stimulation energy may be in the form of low-energy pacing pulses, higher-energy shocking pulses, or the like. When the mounting end 104 is mounted to the intra-cardiac tissue, the electrode 112 is securely affixed to and engages the tissue of interest in order to deliver the stimulation energy directly thereto. In addition to delivering stimulation energy, in an alternative embodiment the electrode 112 may be used to sense electrical activity from the tissue of interest. The electrode 112 may be formed as a single conductive bulb or, alternatively, as a cone, a single wire, or the like. Optionally, the electrode 112 is not covered with insulation material and the conductive material is exposed in order to facilitate a good electrical connection to the local wall tissue. Alternatively, at least a portion of the electrode 112 is covered with insulation to prevent electrical conduction to tissue that engages the insulation.

The mounting end 104 includes a fixation screw 114 securely attached thereto and projecting outward from the mounting end 104. The fixation screw 114 is configured to extend into the tissue of interest to anchor the LIMD 100 to the intra-cardiac tissue. The fixation screw 114 is configured to be screwed into the tissue to firmly adhere the LIMD 100 thereto by pressing the mounting end 104 against the tissue and rotating the LIMD 100 in a first, coupling direction. The fixation screw 114 may be extracted from the tissue by rotating the LIMD 100 in an opposite, uncoupling direction in conjunction with a slight tugging force directed away from the myocardial wall. The fixation screw 114 may be shaped as a helical corkscrew that defines a center channel. For example, the fixation screw 114 may surround the electrode 112 such that the electrode 112 is within the center channel. In an alternative embodiment, the fixation screw 114 is part of the electrode 112. For example, the electrode 112 may have helical threads on an outer surface of the electrode 112, such that the electrode 112 forms the fixation screw 114.

In one or more alternative embodiments, the LIMD 100 may include at least one additional cathode electrode similar to the electrode 112. The additional electrode may extend from the mounting end 104 or from a side of the shell 108. The additional electrode may be configured to directly engage a different tissue of interest than the electrode 112. For example, as shown in FIG. 1, the electrode 112 of the LIMD 100 engages the septum 45 between the right ventricle 37 and the left ventricle 40, while the additional electrode may engage myocardial tissue of the right atrium 30, for example. Thus, the LIMD 100 may be configured to provide stimulation energy to at least two different tissues of interest.

The housing 102 retains a power supply 116 and various electronic components that receive electrical current from the power supply 116. The electronic components provide the functionality of the LIMD 100, such as controlling the stimulation energy delivered to the electrode 112 and sensing the depolarization along the tissue of interest in response to a pacing pulse or to an intrinsic heartbeat. The power supply 116 stores charge for gradual disbursal to the electronic components as needed. The power supply 116 may be a battery. The power supply 116 has a fixed amount of charge at full capacity. The power supply 116 may be rechargeable in some embodiments, and may not be rechargeable in other embodiments. The power supply 116 is fully retained within and surrounded by the housing 102.

In the illustrated embodiment shown in FIG. 2, the electronic components include a pulse generator 118, a processor 120, a memory 122, and a sensing circuit 124. The illustration in FIG. 2 is intended as an overview of the electronic components only, and the electronic components according to an embodiment of the LIMD 100 are described in more detail below with reference to FIG. 5. The pulse generator 118 provides stimulation energy to the electrode 112 which is delivered to the tissue of interest that the electrode 112 engages. The pulse generator 118 includes circuitry to control the output of stimulation energy directed to the electrode 112. For example, the pulse generator 118 produces lower energy pulses for pacing and higher energy pulses for shocking.

The processor 120 is a controller that controls the flow of charge between the power supply 116, the electronic components (such as the pulse generator 118 and the sensing circuit 124), and the electrodes (such as electrode 112). For example, the processor 120 controls the timing and intensity or magnitude of the stimulation pulses. If multiple electrodes are used to deliver stimulation energy to the intra-cardiac tissue, the processor 120 may synchronize the delivery of the pulses. The processor 120 is communicatively coupled to the pulse generator 118, the sensing circuit 124, the memory 122, and the power supply 116. The processor 120 controls the flow of charge based on input information received from the sensing circuit 124. The processor 120 also functions based on instructions stored locally in the memory 122. The memory 122 is a non-transitory tangible computer readable storage medium. The memory 122 stores programmable and executable instructions for the processor 120. The processor 120 is responsive to the programmable instructions to control operation of the LIMD 100. The memory 122 may also store data. Some of the data may be stored prior to completing assembly of the LIMD 100, while other data may be stored during use of the implanted LIMD 100. For example, the memory 122 may be used to store data on intrinsic electrical activity within the heart as monitored by the sensing circuit 124, data on the number, time, and/or magnitude of pacing pulses generated by the pulse generator 118, or the like.

The sensing circuit 124 is configured to monitor intrinsic electrical activity within the heart. The sensing circuit 124 is communicatively coupled to one or more sensing electrodes 126 located on or extending from the housing 102. The sensing electrode 126 is different from the electrode 112, referred to herein as a pulsing electrode 112, because the sensing electrode 126 does not deliver stimulation energy to the intra-cardiac tissue. The sensing electrode 126 is an anode. In the illustrated embodiment, the LIMD 100 includes two sensing electrodes 126 retained on the housing 102. The sensing electrodes 126 are shown located along one or more sides of the shell 108, but may additionally or alternatively be located along the second end 106 of the housing 102. The sensing electrodes 126 sense electrical activity, such as physiologic and pathologic behavior and events, and provide sensed signals to the sensing circuit 124 in response. In an alternative embodiment, the pulsing electrode 112 doubles as a sensing electrode, such that the pulsing electrode 112 is used to deliver stimulation pulses and, in-between pulses, monitors the electrical activity within the tissue of interest for the sensing circuit 124. Thus, the LIMD 100 in this alternative embodiment may have fewer than two designated sensing electrodes 126 on the housing 102.

The housing 102 includes a first body portion 128 and a second body portion 130. The second body portion 130 forms the first, mounting end 104 of the housing 102. The first body portion 128 forms the second end 106 of the housing 102. The first and second body portions 128, 130 each form a portion of the shell 108, although the portions may not be equal. The second body portion 130 has a distal end 136 and an opposite proximal end 138. The electrode 112 and the fixation screw 114 are coupled to and extend from the distal end 136 of the second body portion 130. The first body portion 128 also includes a distal end 140 and an opposite proximal end 142.

The first and second body portions 128, 130 are mated to one another at a detachable interface 132. The detachable interface 132 is defined by the distal end 140 of the first body portion 128 and the proximal end 138 of the second body portion 130. In other words, the distal end 140 of the first body portion 128 mates with the proximal end 138 of the second body portion 130 at the detachable interface 132. The first and second body portions 128, 130 are configured to be un-mated or disengaged from one another at the detachable interface 132 in order to separate the first body portion 128 from the second body portion 130. In FIG. 2, the first and second body portions 128, 130 are shown in a mated position.

Since the electrode 112 and the fixation screw 114 are coupled to the second body portion 130, the second body portion 130 of the housing 102 mounts directly to the intra-cardiac tissue of interest. The first body portion 128 mounts indirectly to the tissue of interest via the second body portion 130. When the LIMD 100 is affixed to the tissue of interest, un-mating the first and second body portions 128, 130 at the detachable interface 132 causes the first body portion 128 to no longer be coupled (e.g., indirectly or directly) to the intra-cardiac tissue. After un-mating, the first body portion 128 is not coupled to either of the second body portion 130 or the intra-cardiac tissue, so the first body portion 128 is not tethered and may be removed from the intra-cardiac chamber. However, the second body portion 130 is configured to remain affixed to the tissue of interest during and after the first body portion 128 is un-mated from the second body portion 130. As used herein, the first body portion 128 is referred to as a "removable component 128" of the housing 102 because the first body portion 128 is configured to be removed relative to the second body portion 130 and relative to the tissue of interest. The second body portion 130 is referred to herein as a "fixed component 130" of the housing 102 because the second body portion 130 is configured to remain affixed to the tissue of interest as the first body portion 128 is un-mated from the second body portion 130 and removed from the intra-cardiac chamber. It is recognized that the term "fixed component" does not mean "permanently" fixed, as the second body portion 130 is configured to be uncouple from the tissue of interest to remove the entire housing 102 from the chamber, if desirable.

The power supply 116 is retained within the removable component 128 of the housing 102. The electrode 112, as mentioned above, is coupled to the fixed component 130 of the housing 102. In order to provide the electrode 112 with electrical current for stimulation (and sensing), current is provided across the detachable interface 132 from the power supply 116 in the removable component 128 to the electrode 112 in the fixed component 130. The current is conveyed across the detachable interface 132 by an energy transfer component (ETC) 134.

The ETC 134 is distributed between the removable and fixed components 128, 130 at the detachable interface 132. The ETC 134 is configured to convey at least one of stimulation energy or sensed signals across the detachable interface 132 when the removable and fixed components 128, 130 are mated to one another. For example, the sensed signals may be transmitted from the electrode 112 or the sensing electrode 126 on the fixed component 130 to the removable component 128 via the ETC 134 for processing. As described further herein, the ETC 134 may transfer energy across the detachable interface 132 via inductive and/or conductive pathways.

As shown in FIG. 2, in one embodiment the electronic control components, such as the pulse generator 118, the processor 120, the memory 122, and the sensing circuit 124, are retained within the removable component 128 along with the power supply 116. Thus, when the removable component 128 is un-mated from the fixed component 130 and removed from the intra-cardiac chamber, the power supply 116 and the listed electronic components are also removed. The removable component 128 also includes a portion of the hardware of the ETC 134. The fixed component 130 may have few, if any, electronic control components. For example, the fixed component 130 may be limited to retaining a portion of the hardware of the ETC 134 and conductors for linking the ETC 134 to the electrodes 112, 126.

When the removable component 128 is removed from the intra-cardiac chamber, the removable component 128 may be extracted from the patient. Since the fixed component 130 remains affixed to the tissue of interest, the LIMD 100 is configured to allow a new, replacement removable component 128 to be implanted into the patient, directed to the intra-cardiac chamber, and subsequently mated to the fixed component 130 at the detachable interface 132. The replacement removable component 128 may have a power supply 116 with more stored charge than the power supply 116 of the removable component 128 that was removed. Thus, one motivation for removing the prior removable component 128 is to replenish the power supply 116. In addition, the replacement removable component 128 may have additional and/or updated electronic components as compared to the electronic components of the prior removable component 128. For example, the processor 120 or the memory 122 in the replacement removable component 128 may be an update version of the processor 120 or the memory 122, respectively, in the prior removable component 128, such that the replacement removable component 128 includes electronic components with addition or enhanced functionality. Furthermore, the replacement removable component 128 may include one or more additional components that were not included in the prior removable component 128, such as a shocking circuit. Thus, another motivation for removing the prior removable component 128 is to update, upgrade, and/or enhance the functionality of the LIMD 100.

In an alternative embodiment, the power supply 116 is disposed within the removable component 128, and the electronic components, such as the pulse generator 118, the processor 120, the memory 122, and the sensing circuit 124, are retained within the fixed component 130. The removable component 128 is replaced in order to replenish the stored charge in the power supply 116. But, since the electronic components are disposed in the fixed component 130, the electronic components remain in the intra-cardiac chamber when the removable component 128 is removed. Replacing the removable component 128 replenishes the power supply 116 but does not update the electronic components, such as the processor 120 and the memory 122. In other alternative embodiments, the electronic components are distributed between the removable component 128 and the fixed component 130 of the housing 102. As one example, the pulse generator 118 and/or the sensing circuit 124 may be retained within the fixed component 130, while the processor 120 and memory 122 may be retained within the removable component 128 along with the power supply 116.

FIG. 3 illustrates a side view of the LIMD 100 showing the removable component 128 disengaged from the fixed component 130 according to an embodiment. For illustrative purposes, portions of the removable and fixed components 128, 130 associated with the ETC 134 are shown in cross-section. Although not depicted, the power supply 116 shown in FIG. 2 is located within the removable portion 128. The electronic components shown in FIG. 2 are located in the removable portion 128, located in the fixed portion 130, or distributed between the removable and fixed portions 128, 130.

In the illustrated embodiment, the ETC 134 includes a transformer that has a first inductive coil 144 and a second inductive coil 146. The first inductive coil 144 is located at least proximate to the distal end 140 of the removable portion 128. For example, in the illustrated embodiment, the first inductive coil 144 extends outward from the distal end 140. The second inductive coil 146 is located at least proximate to the proximal end 138 of the fixed portion 130. In the illustrated embodiment, the second inductive coil 146 extends inwards from the proximal end 138 (e.g., towards the distal end 136) of the fixed portion 130.

To mate the removable component 128 with the fixed component 130, at least one of the components 128, 130 is moved towards the other component along a mating axis 148 until the first inductive coil 144 is proximate to the second inductive coil 146. In an embodiment, the transformer functions via electrical inductance between the first and second coils 144, 146 when the removable and fixed components 128, 130 are mated and an electrical current is conveyed through at least one of the coils 144, 146. For example, electrical current supplied by the power supply 116 (shown in FIG. 2) is directed conductively to the first inductive coil 144. The current through the first inductive coil 144 generates a magnetic field, and the magnetic field induces a current in the second inductive coil 146. The induced current is conveyed conductively from the second inductive coil 146 to the electrode 112, where the electrical current is delivered to the tissue of interest as a stimulation pulse.

The current is transmitted inductively between the removable and fixed components 128, 130, so the coils 144, 146 do not need to mechanically engage each other in order to be electrically connected. Since current from the power supply 116 is directed to the first inductive coil 144 and the second inductive coil 146 receives an induced current, the first inductive coil 144 is referred to herein as a primary coil 144 and the second inductive coil 146 is referred to herein as a secondary coil 146. Although the coils 144, 146 are described as inductively conveying stimulation energy across the detachable interface 132 from the removable component 128 to the fixed component 130, the coils 144, 146 optionally may also be used to inductively transmit sensed signals across the detachable interface 132. An embodiment of the ETC 134 is described in more detail in FIGS. 4A and 4B.

Figure 4A:
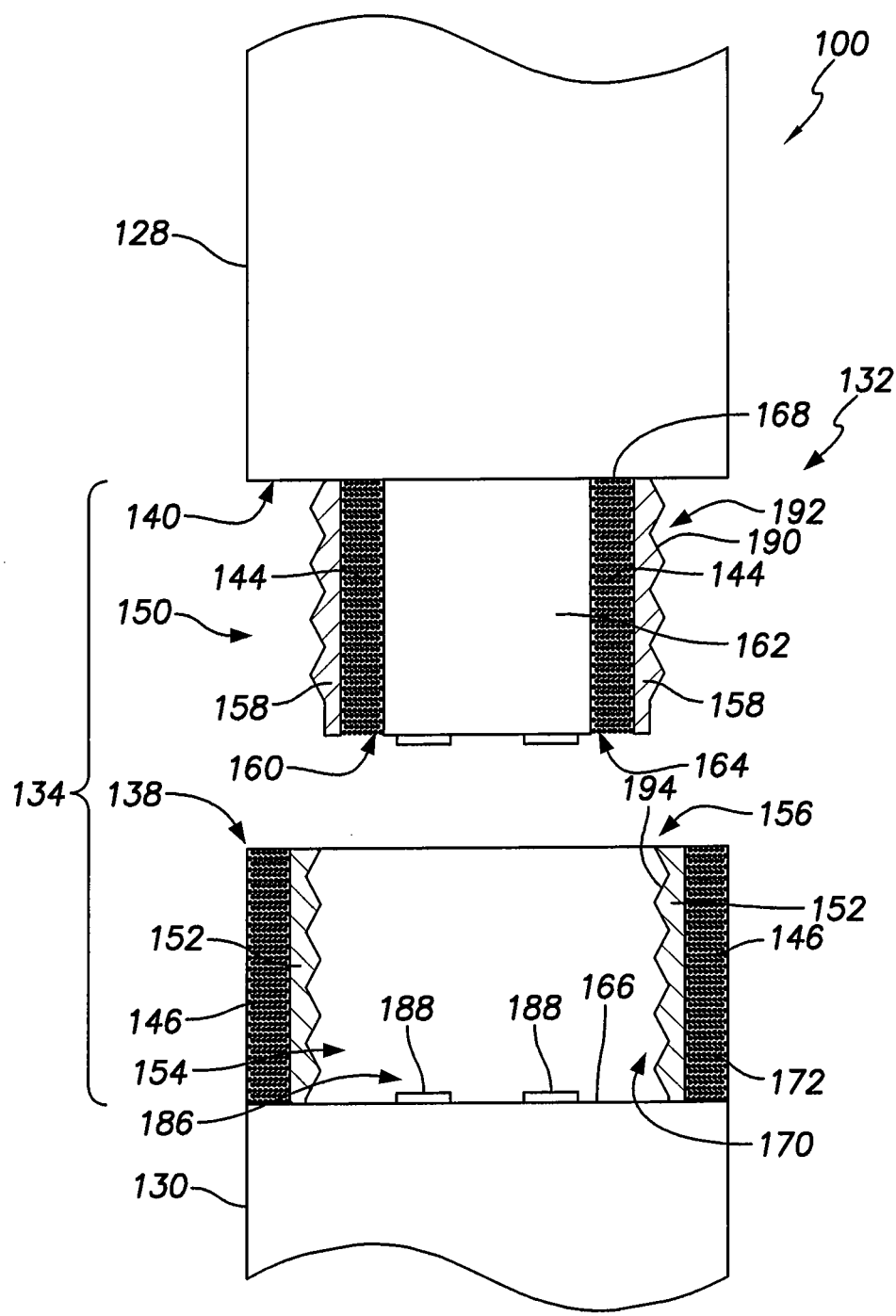
FIGS. 4A and 4B illustrate close-up portions of the removable component and the fixed component of the LIMD in disengaged and mated positions, respectively, according to an embodiment.
Figure 4B:
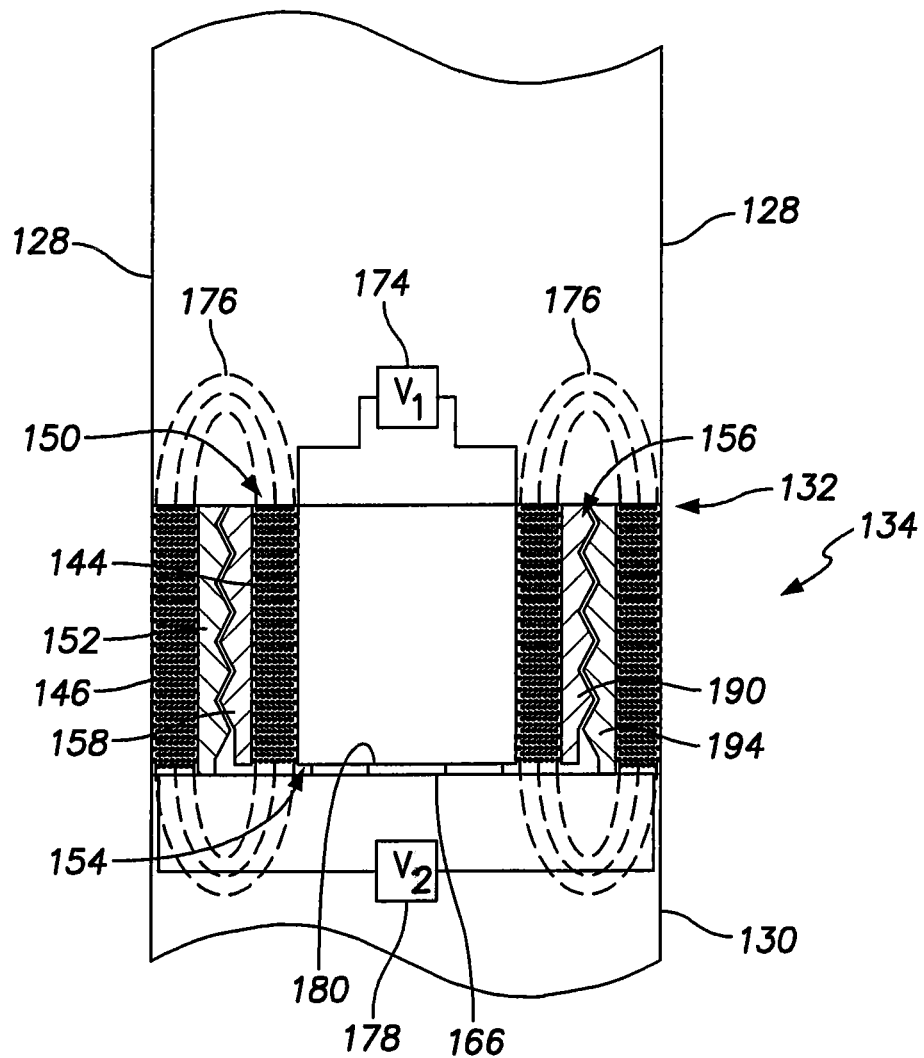

FIGS. 4A and 4B illustrate close-up portions of the removable component 128 and the fixed component 130 of the LIMD 100 in disengaged and mated positions, respectively, according to an embodiment. The removable component 128 is disengaged from the fixed component 130 in FIG. 4A, and the removable component 128 is mated to the fixed component 130 in FIG. 4B. FIGS. 4A and 4B show a close-up view of the detachable interface 132 according to the embodiment shown in FIG. 3.

The detachable interface 132 includes a core 150 positioned at and extending outward from the distal end 140 of the removable component 128. The fixed component 130 includes an outer wall 152 at the proximal end 138 that surrounds and defines a cavity 154. For example, the outer wall 152 may have a curved cross-section that is circular, elliptical, oval, or the like, and the cavity 154 is within the interior of the curved cross-section. The cavity 154 is open to an opening 156 at the proximal end 138. The core 150 is shaped and dimensioned to fit within the cavity 154 when loaded through the opening 156, as shown in FIG. 4B.

In an embodiment, the core 150 includes the primary coil 144 and a sleeve 158. The sleeve 158 may be cylindrical (which is not shown because only a cross-section of the sleeve 158 is illustrated). The sleeve 158 is hollow and defines an interior void 160. The primary coil 144 may be wound or otherwise disposed about an interior perimeter 168 of the sleeve 158. Optionally, the core 150 may further include a cylindrical block 162 centrally located in the void 160, such that the primary coil 144 is disposed radially between the cylindrical block 162 and the sleeve 158. In an alternative embodiment, the core 150 does not include a cylindrical block or any other structure radially interior of the primary coil 144 in the void 160, such that only air is within the void 160 interior of the coil 144.

The primary coil 144 is formed of a conductive material, such as copper or another metal. The coil 144 may be a wire that is wound cylindrically along the interior perimeter 168 of the sleeve 158. For example, the coil 144 may be wound cylindrically along the length of the sleeve 158 from the distal end 140 of the removable portion 128 to a distal end 164 of the sleeve 158. The sleeve 158 is formed of a non-conductive or dielectric material, such as a plastic. Optionally, the sleeve 158 may include a conductive interior that is encased in a non-conductive material, such that the sleeve 158 is electrically insulative. In an embodiment, the cylindrical block 162 is formed of an iron material, such as ferrite.

The outer wall 152 extends from a base surface 166 of the fixed component 130. The cavity 154 is defined along one or more sides by the outer wall 152 and is defined at a distal end by the base surface 166. In the illustrated embodiment, the cavity 154 is undefined at the proximal end due to the opening 156 through which the core 150 is received in the cavity 154. The base surface 166 and an interior perimeter 170 of the outer wall 152 make up interior surfaces that define the cavity 154. The secondary coil 146 may be wound or otherwise disposed about the outer wall 152. In the illustrated embodiment, the secondary coil 146 is wound around an exterior perimeter 172 of the outer wall 152. For example, the secondary coil 146 may not be within the cavity 154. The secondary coil 146 is formed of a conductive material, such as copper or another metal. The coil 146 may be a wire that is wound cylindrically along the length of the outer wall 152 from the proximal end 138 of the fixed portion 130 to the base surface 166. The outer wall 152 is formed of a non-conductive or dielectric material, such as a plastic. Optionally, the outer wall 152 may include a conductive interior that is encased in a non-conductive material, such that the outer wall 152 is electrically insulative.

As shown in FIG. 4, when the removable component 128 is mated to the fixed component 130 at the detachable interface 132, the primary and secondary coils 144, 146 are concentric with one another. For example, the primary coil 144 on the core 150 is radially interior of and surrounded by the secondary coil 146 on the outer wall 152. The primary coil 144 does not mechanically engage the secondary coil 146 because the sleeve 158 and the outer wall 152 extend radially between the coils 144, 146. In this arrangement, the primary and secondary coils 144, 146 are configured to interact to inductively convey at least one of stimulation energy or sensed signals therebetween. For example, when an electrical current is supplied to the primary coil 144 from a power source (V1) 174, the current through the primary coil 144 creates or changes a magnetic field 176 around the primary coil 144 (illustrated as dotted lines), which induces a voltage (V2) 178 in the secondary coil 146. Thus, the ETC 134 is a transformer that uses the coils 144, 146 to transfer electrical energy inductively across the detachable interface 144, 146 without the coils 144, 146 mechanically contacting each other. The power source 174 may be the power supply 116 (shown in FIG. 2). The electrical energy may be stimulation energy that is conveyed from the power source 116 across the detachable interface 132 via the ETC 134 to the electrode 112 (shown in FIG. 2) for delivery to the tissue of interest. It is recognized that induction may also occur from the secondary coil 146 to the primary 144, such as to convey sensed signals from the fixed component 130 to the memory 122 and/or processor 120 (both shown in FIG. 2) in the removable component 128.

The ETC 134 in the illustrated embodiment shows a transformer that has concentric primary and secondary coils 144, 146 that overlap one another during mating, but alternative embodiments may have other arrangements and/or orientations of the coils 144, 146. For example, in one alternative embodiment the primary coil 144 may be spiral-wound (instead of cylindrically wound) and at least partially extends about an end face 180 of the core 150. For example, the end face 150 is at a distal end of the core 150 and is most proximate to the base surface 166 of the fixed component 130 when the core 150 is received in the cavity 154. The spiral-wound coil 144 may be exposed on the end face 150 or at least partially recessed within the end face 150 (such as within a dielectric cover). Like the primary coil 144, the secondary coil 146 may also be spiral-wound and at least partially extends about the base surface 166 of the fixed component 130 (such as exposed on or recessed within the base surface 166). When the removable and fixed components 128, 130 are mated and the core 150 is received within the cavity 154, the coils 144, 146 are positioned axially proximate to one another without mechanically engaging one another. The proximity allows the coils 144, 146 to interact to inductively convey stimulation energy and/or sensed signals therebetween.

Optionally, the ETC 134 forms a conductive path between the removable and fixed components 128, 130 to convey energy therebetween instead of, or in addition to, forming an inductive transformer as described above. For example, referring to FIG. 4A, the core 150 may include a first conductor unit 182 that has at least one conductive contact 184. The conductor unit 182 is disposed on and/or extends from an outer surface of the core 150. The illustrated conductor unit 182 includes two contacts 184 that are disposed on the end face 180 of the core 150. The contacts 184 may be connected to wires that extend through the core 150 to one or more components such as the sensing circuit 124 or the pulse generator 118 (both shown in FIG. 2). The fixed component 130 may include a second conductor unit 186 having at least one conductive contact 188. The second conductor unit 186 is located on and/or extends from an interior surface that defines the cavity 154, such as along the interior perimeter 170 of the outer wall 152 or the base surface 166. In the illustrated embodiment, the second conductor unit 186 includes two contacts 188 that are located on the base surface 166. The two contacts 188 are configured to mechanically and electrically engage the two contacts 184 of the first conductor unit 182 when the core 150 is fully received within the cavity 154. Engagement between the first and second conductor units 182, 186 provides a conductive current path across the detachable interface 132 to conductively convey stimulation energy and/or sensed signals between the components 128, 130.

In an embodiment, the ETC 134 of the LIMD 100 may include both the inductive transformer having the primary and secondary inductive coils 144, 146 and also the first and second conductor units 182, 186 that provide a conductive path, as shown in FIG. 4A. For example, the inductive transformer may be used to provide stimulation energy across the detachable interface 132 from the power supply 116 (shown in FIG. 2) to the electrode 112 (FIG. 2), and the conductive path may be used to provide sensed signals from the sensing electrode 126 (FIG. 2), or another electrode, on the fixed component 130 across the detachable interface 132 to the sensing circuit 124 (FIG. 2) in the removable component 128.

The LIMD 100 includes a retention mechanism in order to retain the removable component 128 and the fixed component 130 in a mated position. The retention mechanism is releasable to disengage the removable component 128 from the fixed component 130 when desired in order to remove and replace the removable component 128. In the illustrated embodiment, the retention mechanism is a threaded connection between the core 150 and the outer wall 152. For example, the core 150 includes a set of first threads 190 that extend along an exterior perimeter 192 of the sleeve 158. The outer wall 152 has a set of second threads 194 that extend along the interior perimeter 170 of the outer wall 152. The first and second threads 190, 194 are helical and complementary. When the core 150 is loaded into the cavity 154, the first threads 190 of the core 150 engage the second threads 194 of the outer wall 152. The removable component 128 is rotated relative to the fixed component 130 such that the helical threads 190, 194 pull the core 150 into the cavity 154 to threadably couple the removable and fixed components 128, 130 to one another. To disengage the removable component 128 from the fixed component 130, the removable component 128 is rotated in an opposite direction relative to the fixed component 130, and the helical threads 190, 194 push the core 150 out of the cavity 154.

In alternative embodiments, instead of or in addition to a threaded coupling, the retention mechanism may include a friction or interference fit, a latching connection, a pin-and-keyhole connection, or the like. For example, instead of the threads 190, 194 shown in FIGS. 4A and 4B being helical as described above, in an alternative embodiment the threads 190, 194 may be alternating ridges and grooves that form a friction and/or latching connection. The ridges may be deflectable, such that as the core 150 is inserted into the cavity 154, the ridges deflect to allow the ridges of the core 150 to pass the ridges of the outer wall 152. Once the core 150 is fully loaded in the cavity 154, the ridges of the core 150 are received in grooves of the outer wall 152. The friction and normal forces between the ridges of the core 150 and the ridges of the outer wall 152 provide retention and resistance against undesired disengagement of the removable and fixed components 128, 130. In another example, the outer wall 152 may include at least one cantilevered deflectable latch that is configured to engage a corresponding catch on the core 150. The base surface 166 of the fixed component 130 in another example may include a pin that extends into the cavity 154 therefrom, and the end face 180 of the core 150 defines a keyhole slot. As the core 150 is loaded into the cavity 154, the pin is received in a wide diameter portion of the keyhole slot. Rotation of the removable component 128 relative to the fixed component 130 causes the pin to move into a small diameter portion of the keyhole slot. The pin may have a bulbous tip that is a larger diameter than the small diameter portion of the keyhole slot, which effectively locks the removable component 128 to the fixed component 130, at least until the removable component 128 is rotated such that the pin is moved into a large diameter portion.

Figure 5:
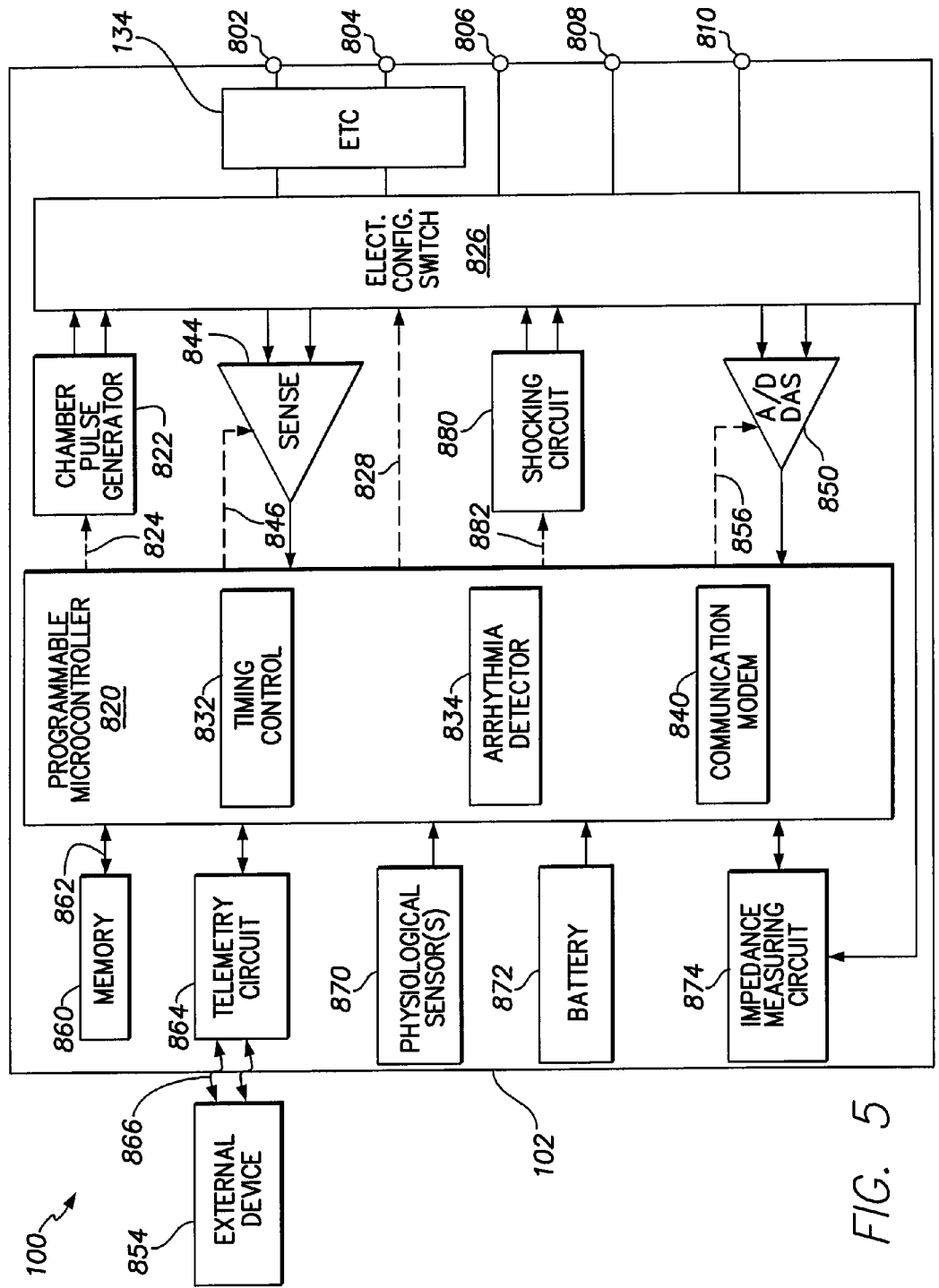
FIG. 5 is a schematic block diagram showing internal components of the LIMD according to an embodiment.

FIG. 5 is a schematic block diagram showing internal components of the LIMD 100 according to an embodiment. In other embodiments, the LIMD 100 may have more or fewer components than are illustrated and described in FIG. 5. In addition, in other embodiments, the LIMD 100 may have a different arrangement of the components, such that some components illustrated as two discrete components may be combined into one single component or vice-versa.

The LIMD 100 has a housing 102 to hold the electronic/computing components. The housing 102 (which is often referred to as the "can", "case", "encasing", or "case electrode") may be programmably selected to act as the return electrode for certain stimulus modes. Housing 102 further includes a plurality of terminals 802, 804, 806, 808, 810 that interface with electrodes of the LIMD 100. Since the LIMD 100 is leadless, the terminals 802-810 may be located at or at least proximate to the electrodes, which are disposed on or extend from the housing 102. The illustrated terminals include: a terminal 802 that connects with a first electrode associated with the housing (e.g. electrode 112 shown in FIG. 2); a terminal 804 that connects with a second electrode associated with the housing (e.g., electrode 126 on the fixed component 130 shown in FIG. 2); a terminal 806 that connects with a third electrode associated with the housing (e.g. electrode 126 on the removable component 128 shown in FIG. 2); and two additional terminals 808, 810 that connect with one or more additional electrodes, if available. The type and location of each electrode may vary. For example, the electrodes may include various combinations of ring, tip, coil and shocking electrodes and the like.

The terminals 802-810 are connected to an electrode configuration switch 826. The switch 826 includes multiple switches for connecting the desired electrodes to the appropriate I/O circuits, thereby facilitating electrode programmability. Some of the electrodes may be located on the fixed component 130 (shown in FIG. 2) of the housing 102, so the ETC 134 may be used to convey power and/or data signals across the detachable interface 132 (shown in FIG. 2) between the switch 826 and the electrodes. For example, pulsing electrode 112 and one sensing electrode 126 (both shown in FIG. 2) are located on the fixed component 130, so terminals 802 and 804 that are associated with these electrodes 112, 126, respectively, are connected to the switch 826 via the ETC 134.

The LIMD 100 includes a programmable microcontroller 820 that controls various operations of the LIMD 100, including cardiac monitoring and stimulation therapy. Microcontroller 820 includes a microprocessor (or equivalent control circuitry), RAM and/or ROM memory, logic and timing circuitry, state machine circuitry, and I/O circuitry. The microcontroller 820 may be or include the processor 120 shown in FIG. 2. The microcontroller 820 includes the ability to process or monitor input signals (data) as controlled by a program code stored in a designated block of memory. The details of the design and operation of the microcontroller 820 are not critical to the invention, and any suitable microcontroller 820 may be used that carries out the functions described herein.

Microcontroller 820 is illustrated as including timing control circuitry 832 to control the timing of the stimulation energy or pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The LIMD 100 further includes a pulse generator 822 that generates stimulation pulses for delivery by one or more electrodes coupled thereto. The pulse generator 822 may be the pulse generator 118 shown in FIG. 2. The pulse generator 822 is controlled by the microcontroller 820 via control signals 824. The pulse generator 822 is coupled to the select electrode(s) via the electrode configuration switch 826. The switch 826 is controlled by control signals 828 from a microcontroller 820. Although only a single pulse generator 822 is illustrated in FIG. 5, optionally the LIMD 100 may include multiple pulse generators similar to pulse generator 822, and each pulse generator may be coupled to one or more electrodes and controlled by the microcontroller 820 to deliver select stimulus pulse(s) to the corresponding one or more electrodes.

The LIMD 100 includes a sensing circuit 844 selectively coupled to one or more electrodes through the switch 826. The sensing circuit 844 may be the sensing circuit 124 shown in FIG. 2. The sensing circuit 844 detects the presence of cardiac activity in certain chambers of the heart. The sensing circuit 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the sensing circuit 844 to sense low amplitude signals. Switch 826 determines the sensing polarity of the cardiac signal by selectively closing the appropriate switches. In this way, the clinician may program the sensing polarity independent of the stimulation polarity.

The output of the sensing circuit 844 is connected to the microcontroller 820 which, in turn, triggers or inhibits the pulse generator 822 in response to the absence or presence of cardiac activity. The sensing circuit 844 receives a control signal 846 from the microcontroller 820 for purposes of controlling the gain, threshold, polarization charge removal circuitry (not shown), and the timing of any blocking circuitry (not shown) coupled to the inputs of the sensing circuitry. Although only a single sensing circuit 844 is illustrated in FIG. 5, optionally the LIMD 100 may include multiple sensing circuits, similar to sensing circuit 844. Each sensing circuit may be coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The LIMD 100 further includes an analog-to-digital (A/D) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The memory 860 may be the memory 122 shown in FIG. 2. The programmable operating parameters used by the microcontroller 820 are stored in memory 860 and used to customize the operation of the LIMD 100 to suit the needs of a particular patient. Such operating parameters define, for example, pacing pulse amplitude, pulse duration, electrode polarity, rate, sensitivity, automatic features, arrhythmia detection criteria, and the amplitude, waveform, and vector of each shocking pulse to be delivered to the patient's heart within each respective tier of therapy.

The operating parameters of the LIMD 100 may be non-invasively programmed into the memory 860 through a telemetry circuit 864 in telemetric communication via communication link 866 with the external device 854. The telemetry circuit 864 allows intracardiac electrograms and status information relating to the operation of the LIMD 100 (as contained in the microcontroller 820 or memory 860) to be sent to the external device 854 through the established communication link 866.

The LIMD 100 can further include magnet detection circuitry (not shown) coupled to the microcontroller 820, to detect when a magnet is placed over the device. A magnet may be used by a clinician to perform various test functions of the LIMD 100 and/or to signal the microcontroller 820 that the external programmer 854 is in place to receive or transmit data to the microcontroller 820 through the telemetry circuits 864.

The LIMD 100 may be equipped with a communication modem (modulator/demodulator) 840 to enable wireless communication with a remote device, such as a second implanted LIMD in a master/slave arrangement, such as described in U.S. Pat. No. 7,630,767. In one implementation, the communication modem 840 uses high frequency modulation. As one example, the modem 840 transmits signals between a pair of LIMD electrodes, such as between the housing 102 and anyone of the electrodes connected to terminals 802-810. The signals are transmitted in a high frequency range of approximately 20-80 kHz, as such signals travel through the body tissue in fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller 820 as a standalone component.

The LIMD 100 can further include one or more physiologic sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states). Signals generated by the physiological sensors 870 are passed to the microcontroller 820 for analysis. The microcontroller 820 responds by adjusting the various pacing parameters (such as rate, AV Delay, V-V Delay, etc.) at which the atrial and/or ventricular pacing pulses are administered. While shown as being included within the LIMD 100, the physiologic sensor(s) 870 may be external to the device 100, yet still be implanted within or carried by the patient. Examples of physiologic sensors might include sensors that, for example, sense respiration rate, pH of blood, ventricular gradient, activity, position/posture, temperature, minute ventilation, and so forth.

A battery 872 provides operating power to all of the components in the LIMD 100. The battery 872 may be the power supply 116 shown in FIG. 2. The battery 872 is capable of operating at low current drains for long periods of time, and is capable of providing high-current pulses (for capacitor charging) when the patient requires a shock pulse. For example, the battery 872 may be configured to provide pulses in excess of 2 amps at voltages above 2 volts for periods of 10 seconds or more. The battery 872 may also have a predictable discharge characteristic so that elective replacement time can be detected. As one example, the LIMD 100 includes lithium/silver vanadium oxide batteries.

The LIMD 100 further includes an impedance measuring circuit 874. The impedance measuring circuit 874 may be used for impedance surveillance during the acute and chronic phases for proper LIMD 100 positioning or dislodgement. The impedance measuring circuit 874 may also be used for detecting, such as detecting operable electrodes and automatically switching to an operable pair if dislodgement occurs, detecting when the device 100 has been implanted, and detecting the opening of heart valves. Furthermore, the impedance measuring circuit 874 may be used for measuring, such as measuring respiration or minute ventilation, measuring thoracic impedance, measuring stroke volume, and the like. The impedance measuring circuit 874 is coupled to the switch 826 so that the impedance measuring circuit 874 may use any desired electrode.

The LIMD 100 may further include a shocking circuit 880, which is controlled by the microcontroller 820 by way of control signals 882. The shocking circuit 880 generates shocking pulses of low (e.g., up to 0.5 joules), moderate (e.g., 0.5-10 joules), or high energy (e.g., 10 to 40 joules), as controlled by the microcontroller 820. Such shocking pulses are applied to the patient's heart through shocking electrodes, if available on the LIMD 100. It is noted that the shock therapy circuitry is optional and may not be implemented in the LIMD 100, as the various embodiments described above and further below may not be configured to deliver high voltage shock pulses. On the other hand, it should be recognized that the LIMD 100 may be used within a system that includes backup shock capabilities, and hence such shock therapy circuitry may be included in the LIMD 100.

Figures 6, 7:
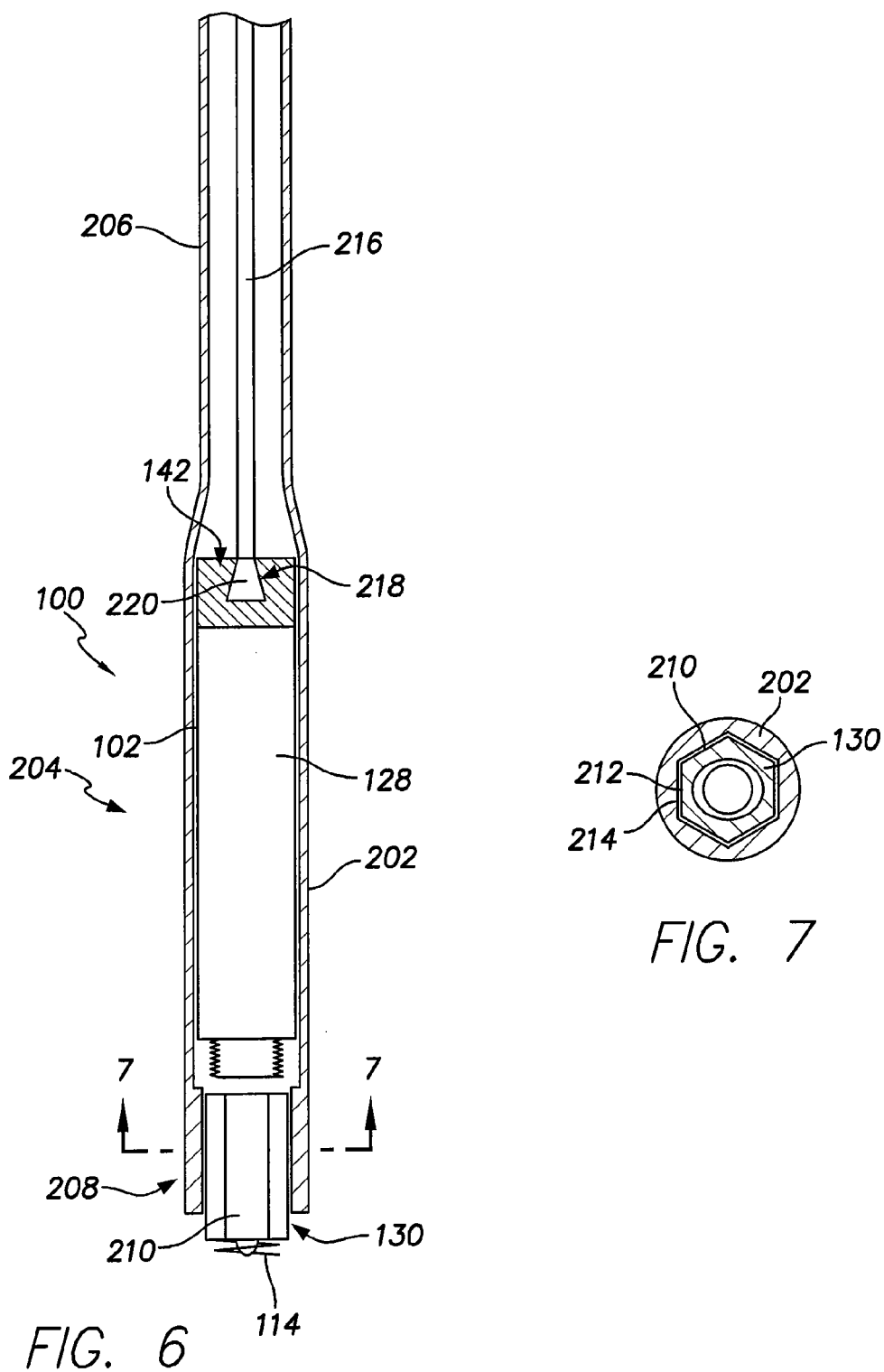
FIG. 6 is a side view of the LIMD within a sheath according to an embodiment.
FIG. 7 shows an axial cross-section view of the fixed component of the LIMD within a distal end of the sheath.

FIG. 6 is a side view of the LIMD 100 within a sheath 202 according to an embodiment. The sheath 202 surrounds the LIMD 100. The sheath 202 is illustrated in cross-section in FIG. 6 to show the LIMD 100 within the sheath 202. In FIG. 6, the proximal end 142 of the removable component 128 of the LIMD 100 is also illustrated in cross-section, while the rest of the LIMD 100 is not shown in cross-section.

In an embodiment, the sheath 202 is used for affixing the LIMD 100 to tissue of interest within the heart of the patient. The sheath 202 is also used for extracting the LIMD 100 from the tissue of interest to remove the LIMD 100 from the heart of the patient, or at least to move to the LIMD 100 to a different tissue of interest or a different chamber of the heart. Affixing and extracting the LIMD 100 is not to be confused with mating and disengaging the removable component 128 of the housing 102 from the fixed component 130. In an embodiment, when the LIMD 100 is initially implanted into the heart using the sheath, the LIMD 100 is whole and includes both the removable component 128 and the fixed component 130 coupled together. When the sheath 202 is used to extract the LIMD 100 from the tissue of interest in the heart, the sheath 202 removes the LIMD 100 as a whole again with both the removable and fixed components 128, 130, unless the removable component 128 has already been removed and not replaced (such that only the fixed component 130 remains in the heart). Thus, in an embodiment, the sheath 202 is configured to engage at least the fixed component 130 of the LIMD 100. If the removable component 128 is mated to the fixed component 130, then the removable component 128 is engaged indirectly by the sheath 202 via the fixed component 130.

The sheath 202 may be a distal region 204 of a catheter 206. For example, the sheath 202 may have a larger diameter than other regions of the catheter 206 in order to receive and surround the LIMD 100. In an embodiment, at least a distal end 208 of the sheath 202 is keyed to an outer or exterior surface 210 of the fixed component 130. Keying the sheath 202 to the outer surface 210 of the fixed component 130 allows the sheath 202 to engage and rotatably couple to the fixed component 130. As used herein, rotatably couple means that rotation of a first object causes like rotation of another object that is rotatable coupled to the first object. In an embodiment, the distal end 208 of the sheath 202 and the outer surface 210 are hexagonally keyed. FIG. 7 shows an axial cross-section view of the fixed component 130 within the distal end 208 of the sheath 202. As shown in FIG. 7, the outer surface 210 has a hexagonal cross-section with six linear sides 212. The interior of the sheath 202 also has six linear surfaces 214 that correspond to the sides 212. Rotation of sheath 202 in one direction causes the fixed component 130 to rotate in the same direction.

Referring back to FIG. 6, the sheath 202 on the catheter 206 is used to transport the LIMD 100 to the chamber and tissue of interest during implantation and also from the tissue and chamber during extraction. As shown in FIG. 6, the fixed component 130 includes the fixation screw 114 which is used to anchor the LIMD 100 to the tissue of interest. Upon providing the fixation screw 114 to the tissue during implantation, since the sheath 202 is keyed to the fixed component 130, rotation of the sheath 202 causes the fixed component 130 to rotate likewise which embeds the fixation screw 114 into the tissue. To extract the LIMD 100, the sheath 202 enters the chamber and is guided around the LIMD 100 such that the distal end 208 engages the fixed component 130. Thereafter, rotation of the sheath 202 in an opposite direction from implantation backs the fixation screw 114 out of the tissue of interest, which eventually disconnects the LIMD 100 from the intra-cardiac tissue, and allows the sheath 202 to be extracted with the LIMD 100 therein.

As shown in FIG. 6, the removable component 128 is disengaged from the fixed component 130. In an embodiment, the removable component 128 is configured to threadably couple to the fixed component 130, such that relative rotation between the components 128, 130 is used to mate and disengage the components 128, 130 depending on the direction of rotation. In an embodiment, the removable component 128 is configured to be mechanically engaged by and rotatably coupled to a gripping device 216 within the sheath 202. When coupled to the removable component 128, the gripping device 216 is configured to be rotated relative to the sheath 202 to rotate the removable component 128 relative to the fixed component 130 (which is rotatably coupled to the sheath 202). Thus, if the sheath 202 is prohibited from rotation, rotation of the gripping device 216 rotates the removable component 128 without rotating the fixed component 130 relative to the tissue of interest to which the fixed component 130 is anchored. Depending on the direction of rotation, the gripping device 216 (and the sheath 202) may be used to mate and un-mate the removable and fixed components 128, 130. The gripping device 216 extends through the catheter 206 and is used to pull the removable component 130 out of the heart and also to move a new replacement removable component 130 into the heart.

In the illustrated embodiment, the gripping device 216 is a push rod. The gripping device 216 extends into a channel 218 at the proximal end 142 of the removable component 128. The proximal end 142 is shown in cross-section to illustrate the channel 218 and the gripping device 216 therein. The end of the gripping device 216 includes a locking collet 220 which is capable of modifying its size and diameter between at least a large size and a small size. In an embodiment, the locking collet 220 is in the small size upon entering the channel 218, and the locking collet 220 transitions to the large size once in the channel 218. When the locking collet 220 is in the large size, the gripping device 216 is mechanically and rotatably coupled to the removable component 128. In alternative embodiments, instead of a locking collet 220 in a channel 218, the gripping device 216 may selectively couple to the removable component 128 via a pin-in-keyhole connection or the like.

Figure 8:
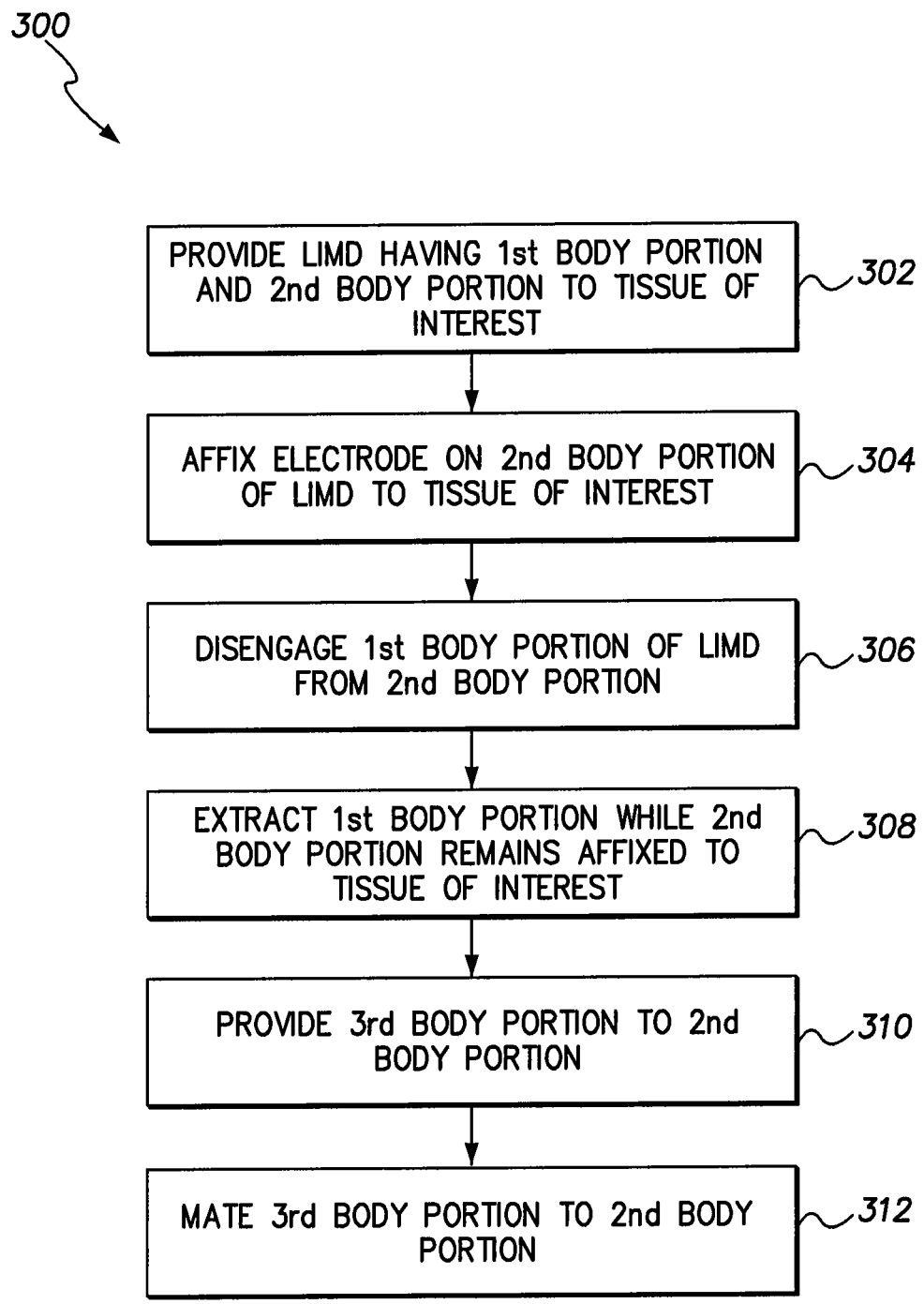
FIG. 8 is a method for use with a LIMD that involves implantation and at least partial extraction of the LIMD from intra-cardiac tissue of a patient.

FIG. 8 is a method 300 for use with a LIMD. The method 300 involves implantation and at least partial extraction of the LIMD from intra-cardiac tissue of a heart of a patient. The method 300 is used to extend the operational life of the LIMD, to enhance the capabilities of the LIMD, and/or to reduce health risks involved when a first LIMD is extracted from the heart of a patient and a replacement LIMD is implanted in the heart. The method 300 may be used in conjunction with the LIMD 100 described above.

At 302, a LIMD having a first body portion and a second body portion is provided to a tissue of interest. The tissue of interest may be intra-cardiac tissue in a chamber of a heart. The first body portion is a removable component of a housing, and the second body portion is a fixed component of the housing. The first and second body portions are mated to one another at a detachable interface. The second body portion is coupled to an electrode. The LIMD may further include an energy transfer component distributed between the first and second body portions at the detachable interface. The energy transfer component is configured to convey at least one of stimulation energy or sensed signals across the detachable interface when the first and second body portions are mated to one another.

At 304, the electrode of the second body portion is affixed to the tissue of interest to anchor the LIMD to the tissue of interest. Upon anchoring the LIMD to the tissue of interest, the LIMD may provide stimulation pulses to the tissue of interest via the electrode and/or may monitor intrinsic electrical activity through the tissue of interest via the electrode or another electrode. The electrode may be affixed via a screw on or near the electrode. Once the LIMD is affixed to the tissue of interest, the LIMD may provide stimulation energy to the tissue of interest in the form of pulses and/or shocks. The LIMD also may monitor intrinsic electrical activity through the tissue of interest.

At 306, the first body portion is disengaged from the second body portion at the detachable interface. The first and second body portions may be threadably coupled to one another, such that the first body portion is disengaged by rotating the first body portion relative to the second body portion (or vice-versa).

At 308, the first body portion is extracted while the second body portion remains affixed to the tissue of interest. The first body portion may be extracted from a chamber of a heart.

At 310, a third body portion is provided to the second body portion that remains affixed to the tissue of interest. The third body portion may be a replacement for the first body portion. For example, the first body portion may include a battery or another power source that provides power to the energy transfer component in the LIMD. The battery of the first body portion may be depleted, and the third body portion may include a new battery or other power source that has more stored energy than the depleted battery.

At 312, the third body portion is mated to the second body portion. The second and third body portions may be mated by a threaded connection or by other retention mechanisms, such as a deflectable latching connection, a friction fit, or a pin-in-keyhole connection. The third body portion includes a power supply and may also include update control components that enhance the functionality of the LIMD. During and after mating the third body portion to the second body portion, the second body portion may remain affixed to the tissue of interest. Once the third body portion is mated to the second body portion, the LIMD may once again function by delivering stimulation energy and monitoring electrical activity.

It is to be understood that the above description is intended to be illustrative, and not restrictive. For example, the above-described embodiments (and/or aspects thereof) may be used in combination with each other. In addition, many modifications may be made to adapt a particular situation or material to the subject matter of an embodiment described herein without departing from scope of the teachings herein. While the dimensions, types of materials and coatings described herein are intended to define parameters of one or more embodiments, they are by no means limiting and are exemplary embodiments. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

What is claimed is:

1. A leadless implantable medical device (IMD) comprising:
   a pulse generator configured to provide stimulation energy for delivery to a tissue of interest;
   a power supply;
   a memory storing programmable instructions;
   a processor communicatively coupled to the memory, the processor responsive to the programmable instructions to control operation of the leadless IMD;
   an electrode configured to be securely affixed to the tissue of interest;
   a housing retaining the pulse generator, the power supply, the memory, and the processor, the housing including first and second body portions mated to one another at a detachable interface, wherein the detachable interface includes a core positioned at and extending outward from a distal end of the first body portion, the second body portion including an outer wall surrounding a cavity open to an opening at a proximal end of the second body portion, the core being shaped and dimensioned to fit within the cavity when loaded through the opening at the proximal end and wherein the electrode is coupled to the second body portion; and
   wherein the core includes a first inductive coil, the second body portion including a second inductive coil at least partially extending about the outer wall around the cavity, the first and second inductive coils being positioned concentric with one another when the first and second body portions are mated to one another, such that the first and second inductive coils interact to inductively convey at least one of stimulation energy or sensed signals therebetween forming an energy transfer component when the first and second body portions are mated to one another.

2. The leadless IMD of claim 1, wherein the pulse generator, the power supply, the memory, and the processor are located within the first body portion which represents a removable component to be disengaged from the second body portion at the detachable interface.

3. The leadless IMD of claim 1, wherein the power supply is located within the first body portion which represents a removable component to be disengaged from the second body portion at the detachable interface, the pulse generator, the memory, and the processor being located within the second body portion which represents a fixed component to remain attached to the tissue of interest after the first body portion is unmated from the second body portion.

4. The leadless IMD of claim 1, wherein the electrode extends from a distal end of the second body portion, the second body portion further includes a fixation screw extending from the distal end, the fixation screw configured to extend into the tissue of interest to anchor the second body portion thereto, the second body portion representing a fixed component to remain attached to the tissue of interest after the first body portion is unmated from the second body portion.

5. The leadless IMD of claim 1, wherein the outer wall of the second body portion extends from a base surface that defines a distal end of the cavity, the core including a first inductive coil that is spiral-wound and at least partially extending about an end face of the core, the second body portion including a second inductive coil that is spiral-wound and at least partially extending about the base surface, the first and second inductive coils being positioned axially proximate to one another when the first and second body portions are mated to one another, such that the first and second inductive coils interact to inductively convey at least one of stimulation energy or sensed signals therebetween.

6. The leadless IMD of claim 1, wherein the core includes a first conductor unit having at least one conductive contact disposed at least one of on or extending from an outer surface of the core, the second body portion including a second conductor unit having at least one conductive contact disposed at least one of on or extending from an interior surface defining the cavity, the first and second conductor units being configured to mechanically engage one another when the first and second body portions are mated to one another, such that the first and second conductor units provide a conductive current path to conductively convey at least one of stimulation energy or sensed signals therebetween.

7. The leadless IMD of claim 1, wherein the electrode is a pulsing electrode that delivers stimulation energy to the tissue of interest, the IMD further comprising at least one sensing electrode located on the second body portion, the at least one sensing electrode configured to monitor intrinsic electrical activity through the tissue of interest.

8. The leadless IMD of claim 1, wherein the detachable interface includes a core positioned at a distal end of the first body portion and an outer wall surrounding a cavity at a proximal end of the second body portion, the core having first threads extending along an outer perimeter thereof, the outer wall having second threads extending along an interior perimeter thereof, wherein the core is shaped and dimensioned to fit within the cavity when the first body portion is mated to the second body portion and the first threads are configured to engage the second threads to threadably couple the first and second body portions to one another.

9. The leadless IMD of claim 1, wherein the first body portion is mechanically and removably coupled to the second body portion via at least one of a threaded connection, a friction fit, a latching connection, or a pin-and-keyhole connection.

10. The leadless IMD of claim 1, wherein the IMD is configured to be surrounded by a sheath, a distal end of the sheath being keyed to an outer surface of the second body portion to engage and rotatably fix the sheath to the second body portion, such that rotation of the sheath causes rotation of the second body portion, wherein the sheath is configured to be rotated to at least one of threadably fix the second body portion to the tissue of interest or threadably remove the second body portion from the tissue of interest.

11. The leadless IMD of claim 10, wherein the first body portion is threadably coupled to the second body portion at the detachable interface, the first body portion being configured to be mechanically engaged by and rotatably coupled to a gripping device within the sheath, wherein the gripping device is configured to be rotated relative to the sheath to rotate the first body portion relative to the second body portion without rotating the second body portion relative to the tissue of interest.

* * * * *